US009207190B2

(12) United States Patent
Steckenrider

(10) Patent No.: US 9,207,190 B2
(45) Date of Patent: Dec. 8, 2015

(54) METHOD FOR NONDESTRUCTIVE TESTING OF OPTICAL DISCONTINUITIES IN MONOLITHIC TRANSPARENT POLYCRYSTALLINE CERAMIC ARTICLES

(71) Applicant: Technology Assessment & Transfer, Inc., Annapolis, MD (US)

(72) Inventor: J. Scott Steckenrider, Hartford City, IN (US)

(73) Assignee: TECHNOLOGY ASSESSMENT & TRANSFER, INC., Annapolis, MD (US)

( * ) Notice: Subject to any disclaimer, the term of this patent is extended or adjusted under 35 U.S.C. 154(b) by 25 days.

(21) Appl. No.: 14/246,054

(22) Filed: Apr. 5, 2014

(65) Prior Publication Data

US 2014/0306114 A1  Oct. 16, 2014

Related U.S. Application Data

(60) Provisional application No. 61/810,292, filed on Apr. 10, 2013.

(51) Int. Cl.
| | |
|---|---|
| G01J 5/02 | (2006.01) |
| G01N 21/958 | (2006.01) |
| G01N 21/17 | (2006.01) |
| G01N 21/3581 | (2014.01) |
| G01N 21/3586 | (2014.01) |

(52) U.S. Cl.
CPC .......... *G01N 21/958* (2013.01); *G01N 21/3581* (2013.01); *G01N 21/3586* (2013.01); *G01N 2021/1734* (2013.01)

(58) Field of Classification Search
CPC ............ G01N 21/958; G01N 2021/1734; G01N 21/3581
USPC ........................................ 250/339.11
See application file for complete search history.

(56) References Cited

U.S. PATENT DOCUMENTS

| | | | |
|---|---|---|---|
| 5,563,702 A | 10/1996 | Emery et al. | |
| 5,790,247 A * | 8/1998 | Henley et al. | 356/237.1 |
| 5,978,078 A | 11/1999 | Salamati-Saradh et al. | |
| 6,396,856 B1 | 5/2002 | Sucha et al. | |
| 6,778,271 B2 | 8/2004 | Catterall et al. | |
| 8,582,094 B1 | 11/2013 | Shortt et al. | |
| 2005/0259247 A1* | 11/2005 | Cyr et al. | 356/239.1 |
| 2010/0195090 A1* | 8/2010 | Ohtake | 356/51 |

* cited by examiner

*Primary Examiner* — David Porta
*Assistant Examiner* — Meenakshi Sahu

(57) ABSTRACT

A method of non-destructive detection of solid inclusions with varying sensitivities but highly congruent positional identification by both short-wavelength and long-wavelength methods. The short-wavelength method consists of lateral scatter (LS) and the long-wavelength method consists of THz imaging. The LS method was able to detect all agglomerated inclusions, transparency variations, voids, and localized phase differences. The THz imaging was able to routinely detect solid inclusions and index inhomogeneity. In combination, the LS and THz imaging methods were able to detect all relevant types of material variation, so that the combination of the two non-destructive testing methods provides a solution capable of detecting the full array of critical material variations in transparent polycrystalline ceramic materials.

19 Claims, 1 Drawing Sheet

METHOD FOR NONDESTRUCTIVE TESTING OF OPTICAL DISCONTINUITIES IN MONOLITHIC TRANSPARENT POLYCRYSTALLINE CERAMIC ARTICLES

This application claims priority to provisional U.S. Application No. 61/810,292, filed Apr. 10, 2013.

This invention was made with government support under Contract No. W31P4Q-11-C-0327 awarded by U.S. Army Contracting Command—Redstone. The government has certain rights in this invention.

FIELD OF THE INVENTION

The present invention generally relates to methods for the inspection of highly transparent ceramic components, and specifically to nondestructive methods for characterizing scattering sources and optical discontinuities in monolithic, transparent, polycrystalline ceramic articles of sizeable thicknesses prior to final polishing.

BACKGROUND OF THE INVENTION

The fabrication of transparent, polycrystalline ceramic articles such as magnesium aluminate (spinel) and aluminum oxynitride (ALON), yttrium oxide, etc. by hot pressing and pressureless sintering has long been known and used as prior art. For example, over 50 patents exist that describe in considerable depth the methods used to produce transparent spinel by either or both hot pressing and pressureless sintering methods. Many of these patents include hot isostatic pressing (HIPing) as the final step needed to achieve near theoretical density and the maximum in-line transmission over the transmission range from 0.2 to 6 µm.

There is, however, very little prior art specifically addressing the characterization of these articles prior to final polish. Because the primary applications for these materials specifically target their broad-spectrum transmittance of electromagnetic (E-M) waves, such characterization must also primarily focus on the E-M properties of the material. Given the imaging applications for these articles, of particular interest are transparency variations (such as haze) and material discontinuities (such as solid or agglomerated inclusions, voids or localized phase differences) with a size on the order of 1 mm or less that degrade the transmission and overall optical quality of the finished, transparent ceramic articles, as well as overall non-uniformity of dielectric properties (i.e., refractive index). The most common methods used for the nondestructive evaluation of ceramic materials are ultrasonic reflectometry (in which the magnitude and timing of reflected or transmitted ultrasonic acoustic pulses are used to interrogate the material uniformity and/or variability) and x-ray radiography (in which material inhomogeneities are detected by their differing radiographic density). However, these methods either are not electromagnetic in nature (ultrasound) or interact with the material at a frequency and with a wavelength dramatically different than that of the spectrum and feature sizes of interest, respectively.

SUMMARY OF THE INVENTION

The present invention provides a method of non-destructive detection of solid inclusions with varying sensitivities but highly congruent positional identification by both short-wavelength and long-wavelength methods. The short-wavelength method consists of lateral scatter (LS) and the long-wavelength method consists of THz imaging. The LS method was able to detect all agglomerated inclusions, transparency variations, voids, and localized phase differences. The THz imaging was able to routinely detect solid inclusions and index inhomogeneity. In combination, the LS and THz imaging methods were able to detect all relevant types of material variation, so that the combination of the two non-destructive testing methods provides a solution capable of detecting the full array of critical material variations in transparent polycrystalline ceramic materials.

OBJECTS AND ADVANTAGES

It is the object of this invention to provide methods for the inspection of highly transparent ceramic components at stages prior to final polish and in thicknesses that range from 0.1 to 1 inch and greater. Transparent, polycrystalline spinel articles are used as examples.

BRIEF DESCRIPTION OF THE SEVERAL VIEWS OF THE DRAWING(S)

Reference is made herein to the accompanying drawings, which are not necessarily drawn to scale, and wherein.

DETAILED DESCRIPTION OF THE PREFERRED EMBODIMENT

The present invention applies the dual techniques of lateral optical scatter and time-domain THz imaging to map the volume of a thick ceramic (spinel) article in three dimensions. Both methods are electromagnetic, thereby probing the material properties of greatest interest for these articles. Lateral optical scatter operates at a wavelength within the transmission spectral range of the spinel (0.532 µm in the current work), while the THz imaging operates at a range of wavelengths in the material (0.03-1.0 mm) comparable to the lateral dimensional resolution required for characterizing these materials. In both cases, the result of the analysis is a three-dimensional volume map of material properties with sub-mm spatial resolution.

Figure 1:
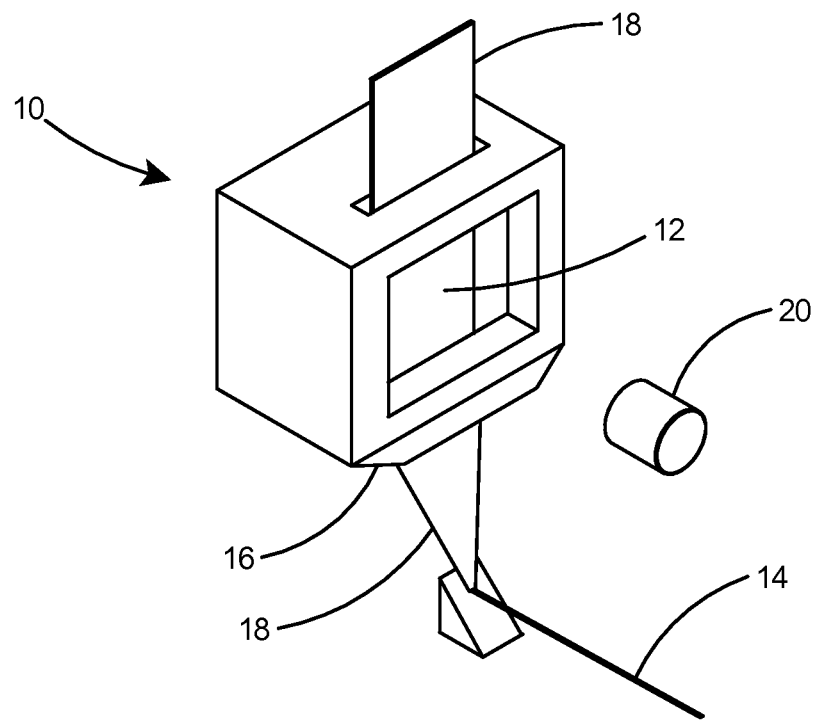
FIG. 1 is a schematic diagram of a Lateral Scatter (LS) inspection method in accordance with embodiments of the invention.

Lateral scatter inspection involves the illumination of the subject article by a thin collimated sheet of light created by laterally sweeping a narrow (i.e., sub-mm) beam of laser light either spatially (through beam expansion by cylindrical lenses) or temporally (through a rapidly rotating mirror). The Lateral Scatter (LS) inspection method 10 depicted in FIG. 1 includes a sample or article 12 illuminated by a laser beam 14, which beam is expanded by lenses 16 to form a light sheet 18 for illuminating the sample while a camera 20 records images of the sample. As shown in FIG. 1, the light sheet 18 illuminates the article 12 cross-sectionally while the camera 20 images the article through its face. If the article surface is rough (i.e., with surface roughness on the order of the illuminating wavelength), the article is surrounded by index-matching fluid and mated to a conjugate form which is polished on its exterior faces and has the same refractive index as the article. The light sheet is then translated through the thickness of the sample (or the sample translated across the light sheet) while the camera digitally records a two-dimensional map of the article's optical properties at each sequential cross-section. These images are then statistically analyzed to identify abnormalities by determining the significance of any variation in Lateral Scatter signature at each point within the cross-section, and these cross-sections are subsequently digitally combined into a fully three-dimensional representation of the optical properties of the article. Because the article will subsequently be ground and polished, a fully three-dimensional map of any abnormalities allows selection of the optimum grinding/polishing depths to achieve maximum component performance post-polish.

Lateral scatter inspection has proven effective in detecting transparency variation, voids, agglomerated inclusions, and localized phase differences with micron-scale sensitivity, and has done so with a positional resolution and precision well below 1 mm. The method has been demonstrated in a wide range of surface finishes, including HIPed, hot-pressed, rough ground and polished with no loss in sensitivity. In addition, it has also proven effective in detecting some solid inclusions, though results here have been inconsistent due primarily to the limited spatial sampling frequencies used during initial examinations.

Figure 2:
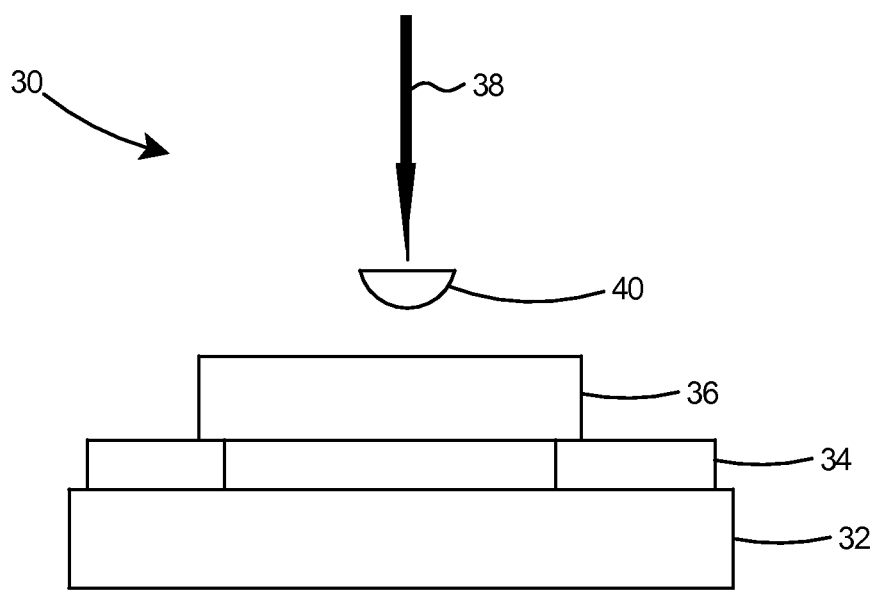
FIG. 2 is a schematic diagram of a pulsed Terahertz (THz) imaging system in accordance with embodiments of the invention.

As illustrated in FIG. 2, THz imaging involves the illumination of an article with focused THz radiation. With reference to FIG. 2, the THz imaging method 30 includes a mirror 32, a spacer 34, the sample or article 36 to be tested, and a THz pulse 38 focused through a lens 40. This radiation is then scattered or reflected by any refractive index interface within the article. The THz detection system measures the amplitude of each scatter/reflection event, and determines its depth either temporally (using short-duration THz pulses) or spectrally (using frequency-swept THz illumination). In the preferred embodiment of temporal depth analysis, the amplitude of each pulse is determined through coherent interference with a time-delayed reference pulse within the electro-optical detection system. By sweeping the time delay for a range of sequential pulses (with a repetition of hundreds of pulses per second) a one-dimensional depth profile of reflection/scattering amplitude can be achieved at each inspection point. When the inspection is mechanically or optically scanned in the other two dimensions, the result is again a full-volume three-dimensional map of dielectric discontinuities within the article.

One particular advantage of the THz component is that, because of the relatively longer wavelength, normal variations in dielectric properties that manifest in sizes well below this wavelength (i.e., ~10 μm or smaller) are transparent to this inspection. This makes THz, ideally suited for articles which have not yet been fully densified, in which the optical analysis is not yet applicable due to a lack of transparency at those wavelengths. As a result, the same would be true for THz inspection of opaque ceramics at any point in their manufacture.

For dense materials in which the size scale of normal dielectric variation is smaller than the optical wavelength (0.532 μm in this case), the resulting THz map can be combined with the aforementioned Lateral Scatter map to arrive at a final characterization of the article comprising its dielectric properties in two separate frequency spectra with sub-mm spatial resolutions.

In addition, the pulsed THz approach also allows for the characterization of both the thickness and the dielectric properties (i.e., refractive index) of the sample. By insuring that the mirror surface is parallel with the scan plane, measuring the arrival times of reflections from the sample's top surface ($t_1$), bottom surface ($t_2$) and the mirror surface ($t_3$), and knowing the nominal thickness of the sample at a reference point ($x_o^r$) one can calculate the thickness at any point on the sample according to the relationship $$x = x_o^r + c[(t_3^r - t_3) - (t_2^r - t_2) + (t_1^r - t_1)] \quad (1)$$

where c is the speed of light and the superscripted r refers to values at the reference point. Similarly, the index of refraction for each point can then be calculated directly as $$n = \frac{c}{v} = \frac{c(t_2 - t_1)}{x} \quad (2)$$

Because thickness is linearly related to each of the six measured arrival times, the resulting precision in thickness determination will be linearly related to the precision in those arrival times, so $\Delta x \approx 2.5 c \Delta t$. Similarly, refractive index varies linearly with two arrival times (those of the front and back surface reflections) and inversely with the thickness determined in Equation 1. As a result, the precision of the index measurement will vary depending on the thickness of sample being characterized.

Although THz imaging proved insensitive to variations in transparency and localized phase differences, it has been effective in detecting solid inclusions with sub-mm positional resolution and precision. Furthermore, it has also demonstrated the ability to spatially map refractive index variations across the plane of the article at a sensitivity of 1-3%, with potential to achieve fractional percentage sensitivity with further optimization. The THz method proved equally effective in working with HIPed, rough ground and polished surfaces, but hot-pressed surfaces limited its effectiveness in mapping index variations due to the scale of surface roughness present in these articles. However, THz imaging's complete insensitivity to even the most severe transparency variation indicates its potential use at points earlier in the manufacturing process (i.e., in sintered or even binder burn-out stages) which lack the optical transparency required for lateral scatter inspection.

In summary, at least one defect type (solid inclusions) was detected with varying sensitivities but highly congruent positional identification in at least some instances by both short- and long-wavelength methods (lateral scatter and THz imaging, respectively). In addition, all agglomerated inclusions, transparency variations, voids, and localized phase differences were detected only by LS, indicating that for these defect types there is no connection between long wavelength and short wavelength properties. Alternatively, only THz imaging is able to routinely detect solid inclusions and index inhomogeneity. Thus, all relevant types of material variation were detected, so that the combination of these two methods provides a solution capable of detecting the full array of critical material variations in transparent polycrystalline ceramic materials.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A nondestructive method of testing for optical discontinuities in a monolithic substantially transparent article comprising:
   A) subjecting the article to a short-wavelength inspection including
      1) laterally sweeping a narrow collimated sub-millimeter (sub-mm) beam of laser light across the article;
      2) digitally recording photographic images at each sequential cross-section illuminated by the collimated beam of laser light;
      3) digitally combining the separate cross-sectional images into a fully three-dimensional lateral scatter (LS) map of the optical properties of the article;
   B) subjecting the article to a long-wavelength inspection including
      1) illuminating the article with focused terahertz (THz) radiation while mechanically or optically scanning the article;
      2) sweeping the time delay for a range of sequential pulses in a first direction to create a one-dimensional depth profile of reflection/scattering amplitude at each inspection point; and
      3) mechanically or optically scanning in the other two dimensions to create a full-volume three-dimensional THz map of dielectric discontinuities within the article; and
   C) combining the LS map with the THz map to arrive at a final characterization of the article comprising its dielectric properties in two separate frequency spectra with sub-mm spatial resolutions.

2. The method of claim 1 wherein said short-wavelength inspection operates at a wavelength within the transmission spectral range of the article.

3. The method of claim 1 wherein the sub-mm wavelength is 0.532 μm.

4. The method of claim 1 wherein the short-wavelength inspection includes a positional resolution below 1 mm.

5. The method of claim 1 wherein the short-wavelength inspection includes creating a two-dimensional map of the optical properties of the article.

6. The method of claim 1 wherein the short-wavelength inspection includes statistically analyzing the images to identify abnormalities.

7. The method of claim 6 wherein identifying the abnormalities includes determining the significance of any variation in lateral scatter signature at each point within the cross-section.

8. The method of claim 1 wherein the THz imaging is operated at a wavelength of 0.03-1.0 mm.

9. The method of claim 1 wherein the THz imaging includes measuring the amplitude of scatter or reflection events through coherent interference with a time-delayed reference pulse.

10. The method of claim 1 wherein sweeping the time delay of the THz radiation for a range of sequential pulses includes a repetition rate of hundreds of pulses per second.

11. The method of claim 1 including combining the THz map with the LS map to arrive at a final characterization of the article comprising its dielectric properties in two separate frequency spectra with sub-mm spatial resolutions.

12. A nondestructive method of testing for optical discontinuities in a monolithic substantially transparent article comprising:
   laterally sweeping a narrow collimated sub-millimeter beam of laser light across the article;
   digitally recording photographic images at each sequential cross-section illuminated by the collimated beam of laser light to record a two-dimensional map of the article's optical properties; and
   digitally combining the separate cross-sectional images into a fully three-dimensional lateral scatter volume map of the optical properties of the article.

13. The method of claim 12 wherein said short-wavelength inspection operates at a wavelength within the transmission spectral range of the article.

14. The method of claim 12 including surrounding the article with index-matching fluid and mating the fluid and article to a conjugate form.

15. A method of testing for optical discontinuities in a monolithic substantially transparent article comprising:
   illuminating the article with focused terahertz (THz) radiation while mechanically or optically scanning the article;
   sweeping the time delay for a range of sequential pulses in a first direction to create a one-dimensional depth profile of reflection/scattering amplitude at each inspection point; and
   mechanically or optically scanning in the other two dimensions to create a full-volume three-dimensional THz map of dielectric discontinuities within the article;
   applying pulsed THz radiation to the article;
   inserting a mirror having a reflective surface parallel with the scan plane and on the opposing side of the article from the pulsed THz radiation;
   measuring the arrival times of reflections from the top surface ($t_1$), bottom surface ($t_2$) and the mirror surface ($t_3$); and
   measuring the nominal thickness of the article at a reference point ($x_o^r$);
   calculating the thickness at any point on the sample according to the relationship $$x = x_o^r + c[(t_3^r - t_3) - (t_2^r - t_2) + (t_1^r - t_1)]$$

where c is the speed of light and the superscripted r refers to values at the reference point; and
   determining the index of refraction of the article for each point according to the relationship $$n = \frac{c}{v} = \frac{c(t_2 - t_1)}{x}$$

where n is the index of refraction.

16. The method of claim 15 wherein the THz imaging is operated at a wavelength of 0.03-1.0 mm.

17. The method of claim 15 wherein the THz imaging includes measuring the amplitude of scatter or reflection events through coherent interference with a time-delayed reference pulse.

18. The method of claim 15 wherein sweeping the time delay of the THz radiation for a range of sequential pulses includes a repetition rate of hundreds of pulses per second.

19. The method of claim 14 wherein said conjugate form has the same refractive index as the article.

\* \* \* \* \*